United States Patent
Grubbs et al.

(10) Patent No.: US 10,470,874 B2
(45) Date of Patent: *Nov. 12, 2019

(54) ADJUSTABLE OPTICAL ELEMENTS WITH ENHANCED ULTRAVIOLET PROTECTION

(71) Applicant: RxSight, Inc., Aliso Viejo, CA (US)

(72) Inventors: Robert H. Grubbs, Pasadena, CA (US); Shiao H. Chang, Arcadia, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,952

(22) Filed: Jul. 20, 2015

(65) Prior Publication Data

US 2017/0020658 A1 Jan. 26, 2017
US 2019/0262125 A9 Aug. 29, 2019

Related U.S. Application Data

(63) Continuation of application No. 11/518,363, filed on Sep. 8, 2006, now Pat. No. 9,119,710.

(60) Provisional application No. 60/715,310, filed on Sep. 8, 2005.

(51) Int. Cl.
*A61F 2/16* (2006.01)
*G02B 5/20* (2006.01)
*A61K 9/00* (2006.01)
*A61L 27/34* (2006.01)

(52) U.S. Cl.
CPC .......... *A61F 2/1613* (2013.01); *A61K 9/0051* (2013.01); *G02B 5/208* (2013.01); *A61L 27/34* (2013.01)

(58) Field of Classification Search
CPC ........ A61F 2/16; A61F 2/1613; A61F 2/1659; A61F 2210/0076; A61F 2250/005; A61F 2250/0053; A61F 2250/0091; A61L 27/34; A61L 27/50; A61L 2430/16; A61L 2400/18; A61L 2430/18
USPC .............. 351/159.24, 159.29, 159.3, 159.32, 351/159.39, 159.59, 159.6, 159.65, 351/159.66
See application file for complete search history.

(56) References Cited

U.S. PATENT DOCUMENTS

| | | | | |
|---|---|---|---|---|
| 4,240,163 A | | 12/1980 | Galin | |
| 4,686,268 A | * | 8/1987 | Kang | .................... C08F 212/14 526/259 |
| 4,803,254 A | * | 2/1989 | Dunks | ........................ A61F 2/16 525/477 |
| 4,822,359 A | * | 4/1989 | Tano | .................... A61F 2/1613 204/192.14 |
| 4,868,251 A | * | 9/1989 | Reich | ..................... C08L 83/04 525/281 |
| 4,985,559 A | | 1/1991 | Goldberg et al. | |

(Continued)

FOREIGN PATENT DOCUMENTS

| | | |
|---|---|---|
| CN | 1161158 | 10/1997 |
| CN | 1371263 | 9/2002 |

(Continued)

*Primary Examiner* — Paul B Prebilic (57) ABSTRACT

The invention relates to novel optical elements having improved UV protection. The optical element comprises a light adjustable optical element with a UV absorbent layer applied to at least one surface of the optical element. The invention is particularly useful in light adjustable intraocular lenses.

13 Claims, 3 Drawing Sheets

(56) References Cited

U.S. PATENT DOCUMENTS

| | | | |
|---|---|---|---|
| 5,729,322 A * | 3/1998 | Collins | C07D 249/20 351/159.02 |
| 5,774,202 A | 6/1998 | Collins | |
| 5,792,822 A * | 8/1998 | Miyabayashi | C08F 2/44 526/240 |
| 6,187,042 B1 * | 2/2001 | Sheets, Jr. | A61L 27/16 623/6.6 |
| 6,406,739 B1 | 6/2002 | LeBoeuf et al. | |
| 6,450,682 B1 | 9/2002 | Lim et al. | |
| 6,613,088 B1 | 9/2003 | Babizhayev | |
| 6,703,466 B1 | 3/2004 | Karakelle et al. | |
| 6,851,804 B2 * | 2/2005 | Jethmalani | A61L 27/48 351/159.01 |
| 6,905,641 B2 | 6/2005 | Platt et al. | |
| 7,441,893 B2 | 10/2008 | Momoda et al. | |
| 8,133,274 B2 | 3/2012 | Zhou et al. | |
| 9,119,710 B2 * | 9/2015 | Grubbs | A61F 2/1613 |
| 2001/0018612 A1 | 8/2001 | Carson et al. | |
| 2001/0025198 A1 * | 9/2001 | Faubl | G02B 1/043 623/6.6 |
| 2001/0025798 A1 | 10/2001 | Andolfatto | |
| 2002/0042653 A1 | 4/2002 | Copeland et al. | |
| 2003/0151831 A1 * | 8/2003 | Sandstedt | A61F 2/1613 359/721 |
| 2003/0174375 A1 | 9/2003 | Jethmalani et al. | |
| 2007/0054131 A1 | 3/2007 | Stewart | |
| 2007/0055369 A1 | 3/2007 | Grubbs et al. | |

FOREIGN PATENT DOCUMENTS

| | | |
|---|---|---|
| CN | 1622969 | 6/2005 |
| EP | 0 282 294 A | 9/1988 |
| WO | WO 2003/058287 | 7/2003 |
| WO | WO 2005/025632 | 3/2005 |

* cited by examiner

Figure 5 Light Transmittance of Lens with and without the UV blocking layer

Figure 6 Light Transmittance of Lens with and without the UV and blue light blocking layer

ADJUSTABLE OPTICAL ELEMENTS WITH ENHANCED ULTRAVIOLET PROTECTION

CROSS-REFERENCE TO RELATED APPLICATIONS

This application is a continuation of U.S. patent application Ser. No. 11/518,363, filed Sep. 8, 2006, now U.S. Pat. No. 9,119,710, which claims priority under 35 U.S.C. § 119(e) to U.S. provisional patent application No. 60/715,310, filed Sep. 8, 2005, the contents of each of which are herein incorporated by reference in their entirety.

STATEMENT REGARDING FEDERALLY SPONSORED RESEARCH OR DEVELOPMENT

Not applicable.

REFERENCE TO A COMPACT DISK APPENDIX

Not applicable.

TECHNICAL FIELD

The present invention relates to light adjustable optical elements with improved UV and/or blue light protection. In the preferred embodiment, a protective layer is placed on at least one surface of the elements. The protective layer has a significantly higher ultraviolet and blue light absorbing properties than the remainder of the optical element.

BACKGROUND OF THE INVENTION

Recent advances in polymer chemistry have lead to the development of novel composition, whose physical and optical characteristics can be altered by exposure to various energy sources such as light. U.S. Pat. No. 6,450,642 discloses the manufacture of optical elements whose optical properties can be manipulated by exposing at least a portion of the element to light, particularly ultraviolet light. The novel materials are particularly useful in the manufacture of intraocular lenses (IOLs) whose optical properties can be manipulated after the IOL has been implanted in a patient.

The materials are prepared by incorporating photopolymerizable macromers into a polymer matrix. Photoinitiators are also incorporated into the matrix. Upon exposure to a specific wave-length of light, the photoinitiator induces the polymerization of the macromers. The polymerization of the macromers causes changes in the physical and optical properties of the optical element, most notable changes in refraction index and/or shape of the material.

In the preferred embodiment, ultraviolet light is used to manipulate the optical properties of the optical element. To prevent premature polymerization of the macromers present, ultraviolet (UV) light absorbers such as benzotriazoles and benzophenones are incorporated in to the optical material. Sufficient UV absorber has been incorporated into the lens that prevents polymerization of the macromers under ambient conditions but allows the use of UV light at relatively safe levels to make the desired adjustments.

While this system has been generally successful, it places limitations on the intensity of the light source used to induce polymerization. This, in turn has been found to limit the rate of polymerization and amount of macromer polymerized, limiting the changes which can be induced in the lens. In addition, the lens still permits some transmission of UV light which, while generally recognized as being within acceptable limits, can potentially cause damage to the interior of the eye.

It would be beneficial to develop a light adjustable optical element whose properties can be adjusted within a range of light intersectors while still offering protection to the users. Specifically, it would be helpful to provide a lens whose properties can be adjusted using UV light but prevents or reduces transmission of UV light through the lens.

SUMMARY OF INVENTION

The invention is an optical element which prevents or reduces the transmission of light or specific wave-lengths of light through the optical element. More specifically, it is an optical element whose properties can be adjusted by exposure of at least a portion of the element to light but that prevents transmission of light completely through the element. In the preferred embodiment, the light is UV light.

In one embodiment, the optical element comprises a region or zone co-extensive with at least one surface of the optical element. The zone contains sufficient light absorber material to prevent or substantially reduce the transmission of light through the zone. In the preferred embodiment, the light absorbing material is a UV absorber such as benzotriazoles or benzophenones. A particularly preferred class of UV absorber is those consisting of one or more UV absorbers linked to a short polymer chain that is compatible with the polymer used to make the optical element. In addition, the light absorbing material can include a blue light blocker, such as a yellow dye.

In one embodiment, the blocking zone is an integral part of the optical element. Alternatively, it can comprise a layer of material that is added to the element at the time or after manufacture.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

The optical elements of the present invention comprise a light adjustable optical element comprising a zone or region which contains sufficient light absorbing material to prevent or substantially reduce the transmission of light or specific wave-lengths of light through the optical element. In one embodiment, the UV blocker zone actually reflects at least a portion of the light back into the main body of the optical element.

In one embodiment, the inventive optical elements comprise a first polymer matrix and a light polymerizable macromers ("macromers") dispersed therein. The first polymer matrix forms the optical element framework and is generally responsible for many of its material properties. The macromers may be a single compound or a combination of compounds that is capable of stimulus-induced polymerization, preferably photo-polymerization. As used herein, the term "polymerization" refers to a reaction wherein at least one of the components of the macromer reacts to form at least one covalent or physical bond with either a like component or with a different component. The identities of the first polymer matrix and the macromers will depend on the end use of the optical element. However, as a general rule, the first polymer matrix and the macromers are selected such that the components that comprise the macromers are capable of diffusion within the first polymer matrix. Put another way, a loose first polymer matrix will tend to be paired with larger macromer components and a tight first polymer matrix will tend to be paired with smaller macromer components.

Upon exposure to an appropriate energy source (e.g., heat or light), the macromer typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element. After exposure, the macromers in the unexposed region will migrate into the exposed region over time. The amount of macromer migration into the exposed region is time dependent and may be precisely controlled. If enough time is permitted, the macromer components will re-equilibrate and redistribute throughout optical element (i.e., the first polymer matrix, including the exposed region). When the region is re-exposed to the energy source, the macromers that have since migrated into the region (which may be less than if the macromer composition were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, the entire optical element is exposed to the energy source to "lock-in" the desired lens property by polymerizing the remaining macromer components that are outside the exposed region before the components can migrate into the exposed region. In other words, because freely diffusable macromer components are no longer available, subsequent exposure of the optical element to an energy source cannot further change its power.

The first polymer matrix is a covalently or physically linked structure that functions as an optical element and is formed from a first polymer matrix composition ("FPMC").

In general, the first polymer matrix composition comprises one or more monomers that upon polymerization will form the first polymer matrix. The first polymer matrix composition optionally may include any number of formulation auxiliaries that modulate the polymerization reaction or improve any property of the optical element. Illustrative examples of suitable FPMC monomers include acrylics, methacrylates, phosphazenes, siloxanes, vinyls, homopolymers and copolymers thereof. As used herein, a "monomer" refers to any unit (which may itself either be a homopolymer or copolymer) which may be linked together to form a polymer containing repeating units of the same. If the FPMC monomer is a copolymer, it may be comprised of the same type of monomers (e.g., two different siloxanes) or it may be comprised of different types of monomers (e.g., a siloxane and an acrylic).

In one embodiment, the one or more monomers that form the first polymer matrix are polymerized and cross-linked in the presence of the macromers. In another embodiment, polymeric starting material that forms the first polymer matrix is cross-linked in the presence of the macromers. Under either scenario, the macromer components must be compatible with and not appreciably interfere with the formation of the first polymer matrix. Similarly, the formation of the second polymer matrix should also be compatible with the existing first polymer matrix. Put another way, the first polymer matrix and the second polymer matrix should not phase separate and light transmission by the optical element should be unaffected.

As described previously, the macromer may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In preferred embodiments, the stimulus-induced polymerization is photo-induced polymerization.

The inventive optical elements have numerous applications in the electronics and data storage industries. Another application for the present invention is as medical lenses, particularly as intraocular lenses.

In general, there are two types of intraocular lenses ("IOLs"). The first type of an intraocular lens replaces the eye's natural lens. The most common reason for such a procedure is cataracts. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) can be precisely calculated. However, in practice, due to errors in measurement of corneal curvature, and/or variable lens positioning and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g., glasses or contact lenses) or cornea surgery. The need for these types of additional corrective measures is obviated with the use of the intraocular lenses of the present invention.

The inventive intraocular lens comprises a first polymer matrix and a macromer dispersed therein. The first polymer matrix and the macromer are as described above with the additional requirement that the resulting lens be biocompatible.

Illustrative examples of a suitable first polymer matrix include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("HPMA"); poly-vinyls such as poly-styrene and poly-vinylpyrrolidone ("PNVP"); poly-siloxanes such as poly-dimethylsiloxane; poly-phosphazenes, and copolymers of thereof U.S. Pat. No. 4,260,725 and patents and references cited therein (which are all incorporated herein by reference) provide more specific examples of suitable polymers that may be used to form the first polymer matrix.

In preferred embodiments, the first polymer matrix generally possesses a relatively low glass transition temperature ("$T_g$") such that the resulting IOL tends to exhibit fluid-like and/or elastomeric behavior, and is typically formed by crosslinking one or more polymeric starting materials wherein each polymeric starting material includes at least one crosslinkable group. Illustrative examples of suitable crosslinkable groups include but are not limited to hydride, acetoxy, alkoxy, amino, anhydride, aryloxy, carboxy, enoxy, epoxy, halide, isocyano, olefinic, and oxime. In more preferred embodiments, each polymeric starting material includes terminal monomers (also referred to as endcaps) that are either the same or different from the one or more monomers that comprise the polymeric starting material but include at least one crosslinkable group. In other words, the terminal monomers begin and end the polymeric starting material and include at least one crosslinkable group as part of its structure. Although it is not necessary for the practice of the present invention, the mechanism for crosslinking the polymeric starting material preferably is different than the mechanism for the stimulus-induced polymerization of the components that comprise the macromer. For example, if the macromer is polymerized by photo-induced polymerization, then it is preferred that the polymeric starting materials have crosslinkable groups that are polymerized by any mechanism other than photo-induced polymerization.

An especially preferred class of polymeric starting materials for the formation of the first polymer matrix is polysiloxanes (also known as "silicones") endcapped with a terminal monomer which includes a crosslinkable group selected from the group consisting of acetoxy, amino, alkoxy, halide, hydroxy, and mercapto. Because silicone IOLs tend to be flexible and foldable, generally smaller incisions may be used during the IOL implantation procedure. An example of an especially preferred polymeric starting material is bis(diacetoxymethylsilyl)-polydimethylsiloxane (which is poly-dimethylsiloxane that is endcapped with a diacetoxymethylsilyl terminal monomer).

The macromer that is used in fabricating IOLs is as described above except that it has the additional requirement of biocompatibility.

The macromer is capable of stimulus-induced polymerization and may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In general, the same type of monomers that is used to form the first polymer matrix may be used as a component of the macromer. However, because of the requirement that the macromer monomers must be diffusable within the first polymer matrix, the macromer monomers generally tend to be smaller (i.e., have lower molecular weights) than the monomers which form the first polymer matrix. In addition to the one or more monomers, the macromer may include other components such as initiators and sensitizers that facilitate the formation of the second polymer matrix.

In preferred embodiments, the stimulus-induced polymerization is photo-polymerization. In other words, the one or more monomers that comprise the macromer each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the macromer includes a photoinitiator (any compound used to generate free radicals) either alone or in the presence of a sensitizer. Examples of suitable photoinitiators include acetophenones (e.g., a-substituted haloacetophenones, and diethoxyacetophenone); 2,4-dichloromethyl-1,3,5-triazines; benzoin methyl ether; and o-benzoyl oximino ketone. Examples of suitable sensitizers include p-(dialkylamino)aryl aldehyde; N-alkylindolylidene; and bis[p-(dialkylarnino)benzylidene] ketone.

Because of the preference for flexible and foldable IOLs, an especially preferred class of MACROMER monomers is poly-siloxanes endcapped with a terminal siloxane moiety that includes a photopolymnerizable group. An illustrative representation of such a monomer is wherein Y is a siloxane which may be a monomer, a homopolymer or a copolymer formed from any number of siloxane units, and X and $X^1$ may be the same or different and are each independently a terminal siloxane moiety that includes a photopolymerizable group. An illustrative example of Y include wherein:
m and n are independently each an integer and
$R^1$, $R^2$, $R^3$, and $R^4$ are independently each hydrogen, alkyl (primary, secondary, tertiary, cyclo), aryl, or heteroaryl. In preferred embodiments, $R^1$, $R^2$, $R^3$, and $R^4$ is a $C_1$-$C_{10}$ alkyl or phenyl. Because macromer monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, $R^3$ are the same and are methyl, ethyl or propyl and $R^4$ is phenyl.

Illustrative examples of X and $X^1$ (or $X^1$ and X depending on how the macromer polymer is depicted) are respectively wherein:

$R^5$ and $R^6$ are independently each hydrogen, alkyl, aryl, or heteroaryl; and Z is a photopolymerizable group.

In preferred embodiments, $R_5$ and $R_6$ are independently each a $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R_5$ and $R_6$ is methyl, ethyl, or propyl and Z is a photopolymerizable group that includes an acrylate or methacrylate moiety.

In especially preferred embodiments, an macromer monomer is of the following formula wherein X and $X_1$ are the same and $R^1$, $R^2$, $R^3$, and $R^4$ are as defined previously.

Illustrative examples of such macromer monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group.

Although any suitable method may be used, a ring-opening reaction of one or more cyclic siloxanes in the presence of triflic acid has been found to be a particularly efficient method of making one class of inventive macromer monomers. Briefly, the method comprises contacting a cyclic siloxane with a compound of the formula in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred macromer monomer.

The inventive IDLs may be fabricated with any suitable method that results in a first polymer matrix with one or more components which comprise the macromer dispersed therein, and wherein the macromer is capable of stimulus-induced polymerization to form a second polymer matrix. In general, the method for making an inventive IOL is the same as that for making an inventive optical element. In one embodiment, the method comprises:

mixing a first polymer matrix composition with a macromer to form a reaction mixture;

placing the reaction mixture into a mold;

polymerizing the first polymer matrix composition to form said optical element; and, removing the optical element from the mold.

The type of mold that is used will depend on the optical element being made. For example, if the optical element is a prism, then a mold in the shape of a prism is used. Similarly, if the optical element is an intraocular lens, then an intraocular lens mold is used and so forth. As described previously, the first polymer matrix composition comprises one or more monomers for forming the first polymer matrix and optionally includes any number of formulation auxiliaries that either modulate the polymerization reaction or improve any property (whether or not related to the optical characteristic) of the optical element. Similarly, the macromer comprises one or more components that together are capable of stimulus-induced polymerization to form the second polymer matrix. Because flexible and foldable intraocular lenses generally permit smaller incisions, it is preferred that both the first polymer matrix composition and the macromers include one or more silicone-based or low $T_g$ acrylic monomers when the inventive method is used to make IOLs.

Figure 1:
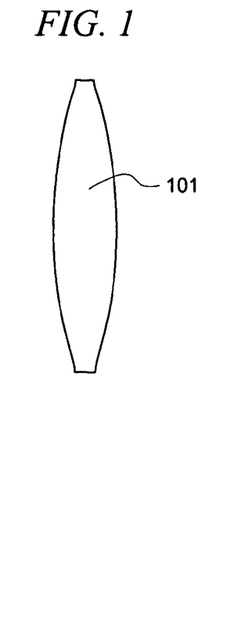
FIG. 1 is a light adjustable optical element without a blocking layer.
Figure 2:
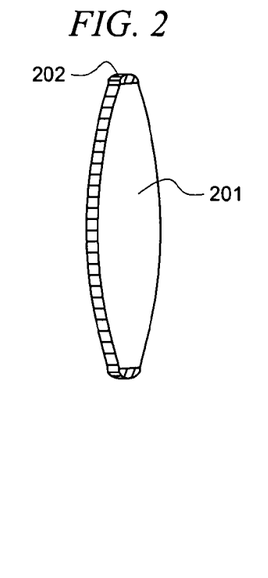
FIG. 2 is a side view of light adjustable optical element of the present invention.
Figure 3:
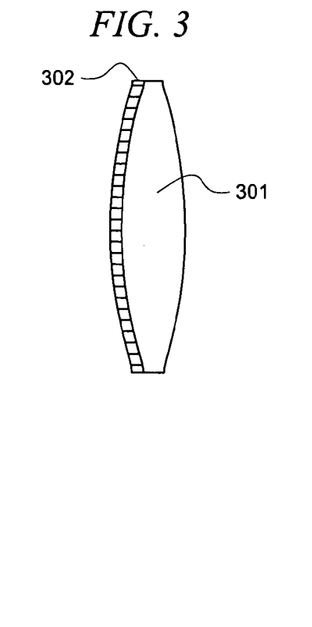
FIG. 3 is a side view of a light adjustable optical element where the blocking layer only extends along the rear surface of the optical element.

In the present invention, a light absorber layer or zone is added to the optical element. The light blocking or absorbent zone is co-extensive with at least one surface of the element, such that it blocks or reduces transmission of a specific wavelength or wavelengths of light through the element. For example, as shown in FIG. 2, the blocking layer 202 extends along the rear and sides of the element. In an alternative embodiment shown in FIG. 3, the blocking layer 302 only extend across the rear surface of the optical element 301. In one embodiment, the blocking zone or layer only affects a specific wave length or wave-lengths of light with ultraviolet light preferred. In another embodiment, the blocking zone or layer could affect both UV light and blue light. This is generally accomplished by incorporation of a light absorbing compound into the blocking region in a sufficient amount to reduce or prevent transmittance through the blocking zone. Thus, while light of a given wavelength can pass through at least a portion of the optical element, the blocking zone prevents passage out from the element. This allows the light to induce polymerization of the macromers described above but prevents the light from exiting or passing completely through the element. This is particularly useful in applications such as light adjustable intraocular lenses. In this application, light, such as UV light, can be used to adjust the optical properties of the lens while the blocking zone prevents passage of the UV light to the interior of the patients' eye. The blocking zone also provides UV protection under ambient conditions.

In one embodiment, ultraviolet absorbing compounds are used. The ultraviolet absorber preferred include benzotriazoles and benzophenone with benzotriazoles most preferred. A particularly useful class of UV absorber consists of at least one UV absorber linked to a short polymer chain. The polymer chain is compatible with the polymers which form the optical element. For example, where the optical element is formed from silica containing polymers, the short chain will also be a silica based polymer.

The amount of absorber should be sufficient to block or reduce the transmission of the target wave-lengths without interfering with the transmission of visible light. The precise amounts will vary depending on such facts as the nature of the absorber used, the compatibility of the absorber with the lens material and the degree of protection desired.

The UV absorber used in the blocking zone may be the same or different than the absorber used in the adjustable portion of the lens. In any event, the amount of UV light transmission allowed by the blocker zone should be significantly less than that in the rest of the lens. In this manner, a relative strong UV source can be used to induce changes in the properties of the lenses but the amount of UV light reaching the retina would be significantly less.

The blocking zone can be created in any one of a number of methods known to those skilled in the art. In one embodiment, the zone is created in conjunction with the formation of the lens itself. In this embodiment, a layer of polymer matrix compatible with the matrix of the lens is formed first and then the remainder of the optical element is formed on top of the blocking zone in a manner similar to that described above. Basically, the thickness of the blocker zone will vary depending on the type of optical element affected. For example, the blocking zone for a light adjustable intraocular lens will range from 0.001 to 250 μm in thickness.

In an alternate embodiment, the blocking zone is formed by applying a polymer layer onto at least one surface of the element. The polymer layer contains the light absorbing material necessary to create the blocking zone or region. Any known method for applying a polymer layer may be used as long as it does not adversely affect the transmission of the desired wave-lengths.

Typical UV absorbers include benzotriazoles, benzophenones and the like. In the preferred embodiment, the photoabsorber is an ultraviolet (UV) absorber. One particularly useful class of UV absorbers is the benzotriazoles having the general structure:

wherein X is independently selected from the group consisting of H, monovalent hydrocarbon radicals and monovalent substituted hydrocarbon radicals preferably containing 1 to about 8 carbon atoms, hydroxyl radicals, amino radicals, carboxyl radicals, alkoxy radicals and substituted alkoxy radicals, preferably containing 1 to 6 carbon atoms and halogen radicals; each $R^1$ is independently selected from the group consisting of H, alkyl radicals, substituted alkyl radicals, alkoxy radicals, substituted alkoxy radicals, preferably containing 1 to 8 carbon atoms, more preferably containing 1 to 4 carbon atoms, comprising either, or more hydroxyl radicals, amino radicals and carboxyl radicals, n is an integer of from 1 to 4 and m is an integer of from 1-3. Preferably, at least one of the X, $R^1$ is other than H. $R^2$ is selected from a moiety comprising vinyl, allyl, alkenyl, substituted alkenyl, alkenoxy, substitute alkenyoxy, acryloxy alkyl, substituted acryloxy, acrylate, methacrylate, and silicone.

Examples of useful monovalent hydrocarbon radicals include alkyl radicals, alkenyl radicals, aryl radicals and the like. Examples of useful alkoxy radicals include methoxy, ethoxy, propyoxy, butoxy, hexoxy and the like. Useful alkyls include methyl, ethyl, propyl, butyl, hexyl, octyl and the like. A particularly useful halogen is chlorine.

The substituted groups referred to herein are exemplified by the above noted groups (and the other groups referred to herein) substituted with one or more substituted groups including elements such as oxygen, nitrogen, carbon, hydrogen, halogen, sulfur, phosphorous and the like and mixtures or combinations thereof. Examples of useful amine groups include $-NH_2$ and groups in which one or both Hs is replaced with a group selected from monovalent hydrocarbon radicals, monovalent substituted hydrocarbon radicals and the like.

It is preferred that no more than one of the Xs is other than H and that no more than one of the $R^1$ is other than H. That is, it is preferred that all or all but one of the Xs. be H and all or all but one of the $R^1$ be H. Such "minimally" substituted benzotriazole moieties are relatively easy to produce and provide outstanding ultraviolet-absorbing properties.

In lieu of ultraviolet absorbers, ultraviolet inhibitors may also be used. UV inhibitors which may be used in the practice of the invention include hindered amines, hydroquinones, methoxy phenones and the like. The compounds may be substituted for the UV absorbers described above.

A particularly useful class of UV-absorbing compounds is selected from compounds having the following formula or structure:

wherein X=chloro and $R^1$=tertiary butyl and $R^2$ has a vinyl group most preferred.

Examples of useful benzotriazoles include 2-(5-Chloro-2H-benzotriazole-2-yl)-6-(1,1-dimethylethyl)-4-ethenylphenol formula:

2-[2'-Hydroxy-3'-t-butyl-5'-(3"-dimethylvinylsilylpropoxy) phenyl]-5-methoxybenzotriazole being the formula:

and 2-(2'-Hydroxy-3'-allyl-5'-methylphenyl)-2H-benzotriazole having the formula:

Another class of UV absorbers that are useful in the practice of the invention are benzophenones including but not limited to 4-allyoxy-2-hydroxy benzophenone having the general formula:

and 4,4'-dallyloxy-2,2'dihydroxybenzophenone having the general structure:

The preferred UV-absorbing compounds absorb UV light strongly in the range of 300 nm to 400 nm, and exhibit reduced absorption at wavelengths higher than about 400 nm.

The amount of UV absorber is that required to give the degree of light absorption desired and is dependent, for example, on the specific UV absorber used, the photoinitiator used, the composition of the element in which UV absorber is to be used, the macromers to be polymerized and the thickness, e.g., optical paths, of the element. By Beers Law of absorption, $A=\epsilon bc$, when A=absorbance, $\epsilon$=extinction coefficient, b=thickness or optical path, and c=concentration of the absorber. The required amount of absorber is inversely proportional to the optical path length or thickness. It is often desired that the UV light transmission at 400 nm be less than 10 to 15% of the incidental light, and at 390 nm be less than 3%.

In addition to the use of a bridged difunction photoinitiator, the UV absorber may also consist of one or more UV absorbers bonded by a short polymer bridge. The photoabsorber have the general formula

$$E-D-E^1$$

wherein E and $E^1$ are UV absorbers and D is a polymer chain with from 2 to 28 monomer moieties or opacifying units. While the formula recited above suggests that the UV absorbers are bonded to the ends of the polymer chains in practice of this invention, the absorber can be bonded at any point along the polymer chain. In addition, when the UV absorber contains more than one allyl or allyloxy groups, the UV absorber may be bonded to more than one polymer bridge. For example, a UV absorber with two allyl structures such as 4,4'diallyloxy, 2,2'-dihydroxy benzophenone may be linked to two polymer bridges. As with the initiator, the polymer bridge should be compatible with if not the same as the material used in the base composition.

In preferred embodiments, the UV absorber will have the general formula:

where $R^{12}$-$R^{16}$ and p is an integer from 1 to 26 are as defined above except that at least one moiety $R^{12}$-$R^{16}$ is a UV absorber and p is an integer from 1 to 26. One silicon bonded photoabsorber useful in the practice of the invention lens is the following structure:

where a and b are integers from 1 to 24 and b is <24.

Another UV absorber structure useful in the practice of the invention is a benzophenone linked to a siloxane backbone having the general formula:

where a and b are integers from 1 to 24 and b is <24.

In the case of a diallylbenzenphenone, the UV absorber may be linked to two polymer bridges such as two siloxane compounds.

The relative amounts of UV absorber and initiator will vary depending upon the desire degree of absorbance for the specific application. Generally the ratio of photoinitiator to UV absorber will range from about 1:1 to about 25:1, with 6:1 to 25:1 preferred. Generally, the relative amounts of photoinitiator and UV absorber can be calculated using the formula:

$$-\log T = A = \epsilon_1 b_1 c_1 + \epsilon_2 b_2 c_2$$

wherein T is transmittance, A is absorbance, $C_1$ is the extinction coefficient of the UV absorber, $b_1$ is the path length of the light and $c_1$ is the concentration of the UV absorber. $\epsilon_2$, $b_2$, and $c_2$ are as defined above except that they relate to the photoinitiator. In practice, it has been found that the actual absorbance is generally less than the predicted values such that the amount use should generally be at least 1.5 times the calculated amount.

EXAMPLES

Example 1

A UV blocking layer was applied to a light adjustable intraocular lens. The layer was approximately 50 μm thick.

Figure 4:
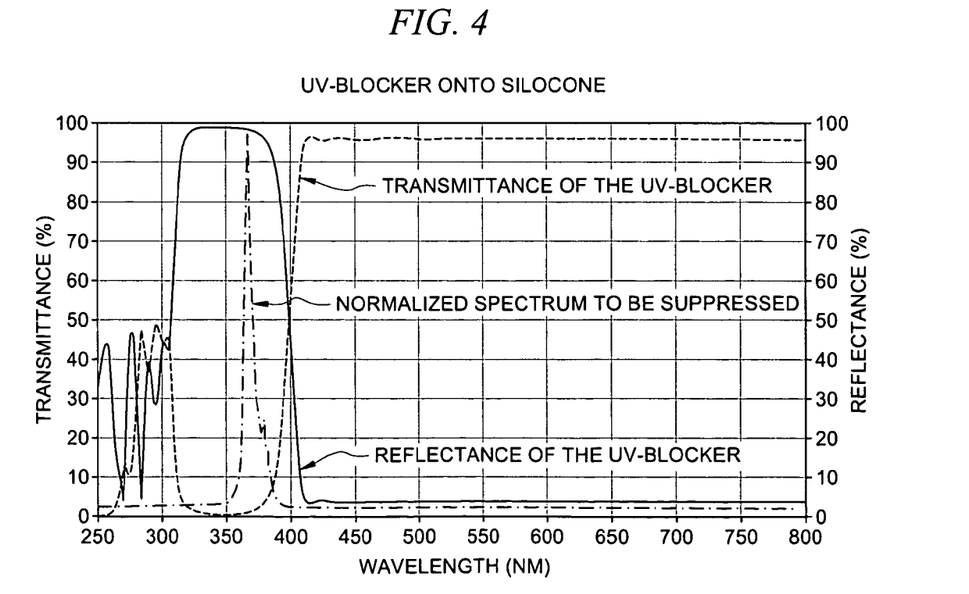
FIG. 4 is a plot of transmittance and reflective curves of a UV blocking zone of the invention.

The lens was then exposed to ultraviolet light at 365 nm. A similar lens without the blocking layer was also exposed to UV light. As shown in FIG. 4, the light transmitted through the lens with the blocking layer at 365 nm was 0.069% as compared to 1.5% for the standard light adjustable lens without the blocking layer. The transmittance at 365 nm was reduced 20 times with the UV blocking layer. was reduced 20 times.

Example 2

A UV and blue light blocking layer was applied to a light adjustable intraocular lens. The layer was approximately 50 μM thick.

Figure 5:
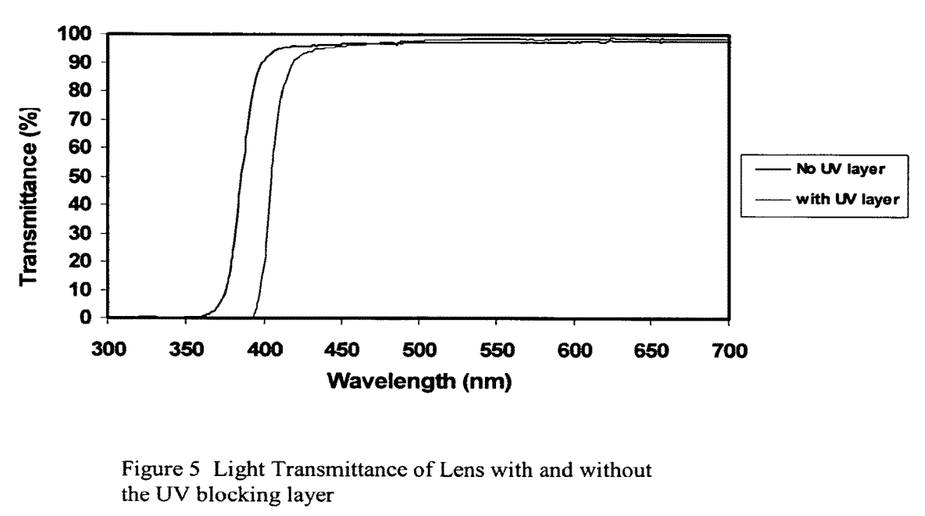
FIG. 5 is a plot of transmittance curve of a blue light blocking zone of the invention.
Figure 6:
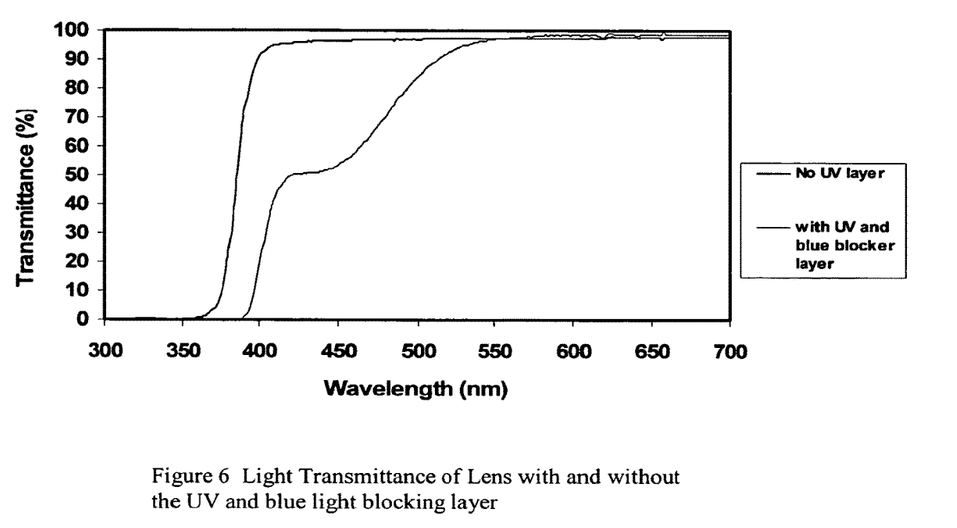
FIG. 6 is a plot of transmittance curve of a UV and blue light blocking zone of the invention.

The lens was then exposed to ultraviolet light at 365 nm. A similar lens without the blocking layer was also exposed to UV light. As shown in FIG. 5, the light transmitted through the lens with the blocking layer at 365 nm was reduced 20 times as compared with the standard light adjustable lens. In addition, significant lower transmittance in the blue light region (390-500 nm) was observed on the lens with the UV and blue light blocking layer.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An intraocular lens, comprising:
   an adjustable optical element, wherein at least one of an optical property and a physical property of the optical element is adjustable by exposure to ultraviolet light; and
   an ultraviolet (UV) absorbing layer that is co-extensive with at least one surface of the adjustable optical element, having a polymeric layer comprising a benzotriazole UV absorber with a formula wherein
   X is selected from the group consisting of a monovalent hydrocarbon radical, a monovalent substituted hydrocarbon radical, a hydroxyl radical, an amino radical, a carboxyl radical, and a halogen radical;
   $R^1$ is selected from the group consisting of H, an alkyl radical, a substituted alkyl radical, an alkoxy radical, a substituted alkoxy radical including a hydroxyl radical, an amino radical, and a carboxyl radical;
   $R^2$ is selected from the group consisting of a vinyl, an allyl, an alkenyl, a substituted alkenyl, an alkenoxy, a substituted alkenyoxy, an acryloxy alkyl, a substituted acryloxy, an acrylate, a methacrylate, and a silicone;
   n is an integer in a range of 1 to 4, and m is an integer in a range of 1 to 3; and
   the ultraviolet absorbing layer comprises a photoinitiator, wherein
      a ratio of the photoinitiator to the benzotriazole UV absorber is in a range of 1:1 to 25:1.

2. The intraocular lens of claim 1, wherein:
   at least one of the substituted hydrocarbon radical, the substituted alkyl radical, the substituted alkoxy radical, the substituted alkenyl, the substituted alkenyoxy, and the substituted acryloxy is substituted with an element selected from the group consisting of oxygen, nitrogen, carbon, hydrogen, halogen, sulfur, phosphorous, and combinations thereof.

3. The intraocular lens of claim 1, wherein:
X is selected from the group consisting of a monovalent hydrocarbon radical, a monovalent substituted hydrocarbon radical, a hydroxyl radical, an amino radical, a carboxyl radical, and a halogen radical, the selected radical having 1 to 8 carbon atoms.

4. The intraocular lens of claim 1, wherein:
$R^1$ is selected from the group consisting of an alkyl radical, a substituted alkyl radical, an alkoxy radical, a substituted alkoxy radical including a hydroxyl radical, an amino radical, and a carboxyl radical, the selected radical having 1 to 8 carbon atoms.

5. The intraocular lens of claim 1, wherein:
a thickness of the UV absorbing layer is in a range of 0.001 to 250 μm.

6. The intraocular lens of claim 1, wherein:
the benzotriazole UV absorber is a UV inhibitor, selected from the group consisting of a hindered amine, a hydroquinone, and a methoxy phenone.

7. The intraocular lens of claim 1, wherein:
the benzotriazole UV absorber has a formula wherein
X is a chloro, $R^1$ is a tertiary butyl, and
$R^2$ is a vinyl group.

8. The intraocular lens of claim 1, the benzotriazole UV absorber comprising:
2-(5-Chloro-2H-benzotriazole-2-yl)-6-(1,1-dimethylethyl)-4-ethenylphenol with a formula 9. The intraocular lens of claim 1, the benzotriazole UV absorber comprising:
2-[2'-Hydroxy-3'-t-butyl-5'-(3"-dimethylvinylsilylpropoxy-) phenyl]-5-methoxybenzotriazole with a formula

10. The intraocular lens of claim 1, the benzotriazole UV absorber comprising:
2-(2'-Hydroxy-3'-allyl-5'-methylphenyl)-2H-benzotriazole with a formula 11. The intraocular lens of claim 1, wherein:
the benzotriazole UV absorber is bonded to a polymer chain.

12. The intraocular lens of claim 11, comprising:
a second UV absorber, bonded to the polymer chain, so that the polymer chain forms a bridge between the benzotriazole UV absorber and the second UV absorber.

13. An intraocular lens, comprising:
an adjustable optical element, wherein at least one of an optical property and a physical property of the optical element is adjustable by exposure to ultraviolet light; and
an ultraviolet (UV) absorbing layer that is co-extensive with at least one surface of the adjustable optical element, having a polymeric layer comprising a benzotriazole UV absorber with a formula wherein
X is a halogen-substituted hydrocarbon radical;
$R^1$ is selected from the group consisting of H, an alkyl radical, a substituted alkyl radical, an alkoxy radical, a substituted alkoxy radical including a hydroxyl radical, an amino radical, and a carboxyl radical;
$R^2$ is selected from the group consisting of a vinyl, an allyl, an alkenyl, a substituted alkenyl, an alkenoxy, a substituted alkenyoxy, an acryloxy alkyl, a substituted acryloxy, an acrylate, a methacrylate, and a silicone; and
n is an integer in a range of 1 to 4, and m is an integer in a range of 1 to 3.

* * * * *